US011260114B2

(12) United States Patent
Abushakra et al.

(10) Patent No.: US 11,260,114 B2
(45) Date of Patent: Mar. 1, 2022

(54) BOTULINUM NEUROTOXINS FOR USE IN THERAPY

(71) Applicant: Bonti, Inc., Madison, NJ (US)

(72) Inventors: Sawsan Abushakra, Madison, NJ (US); Wajdie Ahmad, Madison, NJ (US); Fauad Hasan, Madison, NJ (US); Michael Jarpe, Madison, NJ (US)

(73) Assignee: Bonti, Inc., Madison, NJ (US)

( * ) Notice: Subject to any disclaimer, the term of this patent is extended or adjusted under 35 U.S.C. 154(b) by 0 days.

(21) Appl. No.: 16/496,011

(22) PCT Filed: Mar. 22, 2018

(86) PCT No.: PCT/US2018/023709
§ 371 (c)(1),
(2) Date: Sep. 20, 2019

(87) PCT Pub. No.: WO2018/175688
PCT Pub. Date: Sep. 27, 2018

(65) Prior Publication Data
US 2020/0046814 A1 Feb. 13, 2020

Related U.S. Application Data

(60) Provisional application No. 62/508,215, filed on May 18, 2017, provisional application No. 62/474,749, filed on Mar. 22, 2017, provisional application No. 62/474,744, filed on Mar. 22, 2017.

(51) Int. Cl.
| A61K 38/48 | (2006.01) |
| A61K 8/64 | (2006.01) |
| A61Q 19/00 | (2006.01) |
| C12N 9/52 | (2006.01) |

(52) U.S. Cl.
CPC ............ *A61K 38/4893* (2013.01); *A61K 8/64* (2013.01); *A61Q 19/00* (2013.01); *C12N 9/52* (2013.01); *A61K 2800/91* (2013.01); *C12Y 304/24069* (2013.01)

(58) Field of Classification Search
None
See application file for complete search history.

(56) References Cited

U.S. PATENT DOCUMENTS

| 7,964,199 | B1 | 6/2011 | Bigalke et al. | |
| 8,129,139 | B2* | 3/2012 | Ton | B01D 15/363 435/41 |
| 8,324,349 | B2* | 12/2012 | Ton | B01D 15/362 530/350 |
| 8,357,541 | B2* | 1/2013 | Ton | B01D 15/363 436/161 |
| 8,927,229 | B2* | 1/2015 | Ton | B01D 15/361 435/41 |
| 8,932,827 | B2* | 1/2015 | Ton | B01D 15/362 435/41 |
| 9,206,409 | B2* | 12/2015 | Ton | B01D 15/362 |
| 9,682,195 | B2* | 6/2017 | Tucker | A61M 5/31511 |
| 9,719,076 | B2* | 8/2017 | Ton | B01D 15/363 |
| 10,464,178 | B1* | 11/2019 | Steeb | B23Q 1/015 |
| 10,647,750 | B2* | 5/2020 | Anderson | A61P 25/08 |
| 2006/0051377 | A1* | 3/2006 | First | A61K 38/4893 424/239.1 |
| 2006/0067950 | A1 | 3/2006 | Taylor | |
| 2006/0073208 | A1 | 4/2006 | First | |
| 2010/0121042 | A1* | 5/2010 | Fernandez-Salas | C07K 14/33 536/23.7 |
| 2010/0168023 | A1* | 7/2010 | Ruegg | A61P 17/00 514/8.9 |
| 2011/0008843 | A1* | 1/2011 | Ton | B01D 15/363 435/71.3 |
| 2011/0268765 | A1* | 11/2011 | Ruegg | A61P 17/16 424/247.1 |
| 2012/0123095 | A1* | 5/2012 | Ton | B01D 15/361 530/350 |
| 2012/0225049 | A1* | 9/2012 | Fletcher | A61K 8/606 424/94.63 |
| 2012/0245324 | A1* | 9/2012 | Ton | C12N 9/52 530/350 |
| 2013/0138079 | A1* | 5/2013 | Tucker | A61M 5/3129 604/506 |
| 2014/0308267 | A1 | 10/2014 | Schmidt | |
| 2015/0283045 | A1* | 10/2015 | Hack | A61K 8/25 424/401 |

(Continued)

FOREIGN PATENT DOCUMENTS

| JP | 2011157331 | 8/2011 |
| WO | 02089834 A1 | 11/2002 |

(Continued)

OTHER PUBLICATIONS

Foran et al, JBC, 2003, 178/2:1363-1371 (Year: 2003).*
Hanna et al, American Journal of Clinical Dermatology (2020) 21:157-162. published online: Nov. 28, 2019 (Year: 2020).*
Yoelin et al, Plast. Reconstr. Surg., 142:847e-855e, 2018 (Year: 2018).*
Agarwal etal, Journal of Biological Chemistry, Sep. 19, 2008, 283/38:25944-25951. published, JBC Papers in Press, Jul. 25, 2008 (Year: 2008).*
Eapen, Journal of Cosmetic Dermatology, 2008. 7:221-225 (Year: 2008).*
Shi etal, Human vaccines And Immunotherapeutics, 2020, 16/1:100-108. (Year: 2020).*
Kato, K., et al., Botulinum neurotoxin A2 reduces incidence of seizures in mouse models of temporal lobe epilepsy, Toxicon, 2013, 109-115, 74.

(Continued)

*Primary Examiner* — Nita M. Minnifield
(74) *Attorney, Agent, or Firm* — Brigitte C. Phan

(57) ABSTRACT

Disclosed herein are compositions and methods for use in therapeutic procedures. Use of a "fast-acting" botulinum toxin for cosmetic treatment and/or to prevent or reduce scarring. "Fast-acting" refers to a botulinum toxin that produces effects in the patient more rapidly than those produced by, for example, a botulinum neurotoxin type A. The "fast-acting" botulinum toxin, for example, type E.

18 Claims, 4 Drawing Sheets

(56) References Cited

U.S. PATENT DOCUMENTS

| | | | |
|---|---|---|---|
| 2016/0097045 A1* | 4/2016 | Ton | C07K 14/33 435/220 |
| 2017/0181943 A1* | 6/2017 | Hack | A61K 8/25 |
| 2018/0214717 A1* | 8/2018 | Ruegg | A61P 37/04 |
| 2018/0311333 A1* | 11/2018 | Ruegg | A61P 25/02 |
| 2018/0369348 A1 | 12/2018 | Blumenfeld | |
| 2019/0183987 A1* | 6/2019 | Abushakra | A61K 8/64 |
| 2019/0300583 A1* | 10/2019 | Jarpe | A61K 38/4893 |
| 2020/0023044 A1* | 1/2020 | Abushakra | A61K 9/0019 |
| 2020/0038492 A1* | 2/2020 | Hasan | A61K 9/0019 |
| 2020/0046814 A1* | 2/2020 | Abushakra | A61K 8/64 |
| 2020/0071686 A1* | 3/2020 | Ton | B01D 15/363 |
| 2020/0215357 A1* | 7/2020 | Ruegg | A61P 25/06 |
| 2020/0248223 A1* | 8/2020 | Khan | C12M 41/34 |
| 2021/0060144 A1* | 3/2021 | Brooks | A61K 38/4893 |

FOREIGN PATENT DOCUMENTS

| | | | | |
|---|---|---|---|---|
| WO | 2007044809 A3 | 8/2007 | | |
| WO | 2012135304 A1 | 10/2012 | | |
| WO | 2015126527 A1 | 8/2015 | | |
| WO | WO-2017075468 A1 * | 5/2017 | | A61P 27/02 |
| WO | WO-2018106339 A1 * | 6/2018 | | A61P 21/00 |
| WO | WO-2018175688 A1 * | 9/2018 | | A61K 38/4893 |
| WO | WO-2018175696 A1 * | 9/2018 | | A61P 25/02 |
| WO | WO-2018200991 A * | 11/2018 | | C12N 9/52 |
| WO | WO-2018233813 A1 * | 12/2018 | | C12Y 304/24069 |
| WO | WO-2019005773 A1 * | 1/2019 | | A61K 31/445 |
| WO | WO-2019126322 A1 * | 6/2019 | | A61K 9/0019 |
| WO | WO-2019195454 A1 * | 10/2019 | | C07K 14/33 |

OTHER PUBLICATIONS

Lee, W., et al , Refractory focal motor seizures controlled with intramuscular botulinum toxin, Epilepsy Research, 2017, 93-97, 133.

Mader, E.C., et al., Botulinum Toxin Injections for Simple Partial Motor Seizures Associated with Pain, Case Reports in Medicine, 2012, 4 pgs.

Zhang, X., et al., Extracranial injections of botulinum neurotoxin type A inhibit intracranial meningeal nocicetpors' response to stimulation of TRPVI and TRPAI channels: Are we getting closer to solving this puzzle?, Cephalalgia, 2016, 875-886, 36 (9).

Anonymous, Evaluate Safety and Efficacy of a Single Treatment Cycle of EB-001 in Subjects With Glabellar Frown Lines, ClinicalTrials. gov, Oct. 20, 2016, Retrieved from the Internet:https://clinicaltrials.gov/ct2/show/study/NCT0293932E.

Bonti et al., Bonti Announces Topline Results of EB-001 Phase 2A Clinical Study in Glabellar Lines, BusinessWire.com, Aug. 9, 2017, Retrieved from the Internet:https://www.businesswire.com/news/home/20170809005615/en/Bonti-Announces-Topline-Results-EB-001-Phase-2A.

Neil S. Sadick, Botulinum Toxin Type B for Glabellar Wrinkles: A Prospective Open-Label Response Study, Dermatologic Surgery, 2002, vol. 28, No. 9, pp. 817-821.

Timothy Corcoran Flynn, Use of Intraoperative Botulinum Toxin in Facial Reconstruction, Dermatological Surgery, 2009, vol. 35, No. 2, pp. 182-188.

* cited by examiner

BOTULINUM NEUROTOXINS FOR USE IN THERAPY

CROSS REFERENCE TO RELATED APPLICATIONS

This application is a national stage application under 35 U.S.C. § 371 PCT patent application PCT/US2018/023709, filed on Mar. 22, 2018, which claims priority to and the benefit of U.S. provisional patent application Nos. 62/508,215, filed May 18, 2017, 62/474,749, filed Mar. 22, 2017 and 62/474,744, filed Mar. 22, 2017, hereby incorporated herein by reference in their entireties.

FIELD

The present specification relates to the use of neurotoxins in therapy.

BACKGROUND

Cosmetic or plastic surgery includes surgical and nonsurgical procedures that enhance and reshape structures of the body to improve appearance and confidence. These procedures are becoming increasingly popular.

SUMMARY

Disclosed herein are compositions and methods for use in cosmetic treatments. For example, disclosed embodiments comprise use of a "fast-acting" botulinum toxin to treat, for example, glabellar lines.

Disclosed herein are compositions and methods for use in minimizing scarring. For example, disclosed embodiments comprise use of a "fast-acting" botulinum toxin to reduce muscle tension in the proximity of a wound, thus preventing or reducing scarring.

In embodiments, muscle activity in the proximity of a skin incision or laceration is reduced, thus reducing or preventing scar formation.

In embodiments, disclosed methods comprise additional cosmetic procedures. For example, disclosed embodiments comprise administration of a fast-acting botulinum neurotoxin in combination with, for example, a dermal filler injection, an eye lift, rhinoplasty, or the like.

In embodiments, the botulinum toxin is a "fast-recovery" toxin.

In embodiments, the "fast-acting" botulinum toxin is also a "fast-recovery" toxin.

In embodiments, the cosmetic treatment can comprise a supplemental botulinum administration after an initial administration.

In embodiments, disclosed methods comprise administration of a fast-acting botulinum neurotoxin in combination with, for example, a slower-acting neurotoxin.

In embodiments, disclosed methods comprise administration of a fast-recovery botulinum neurotoxin in combination with, for example, a slower-recovery neurotoxin.

In embodiments, neurotoxin dosage is expressed in protein amount.

DETAILED DESCRIPTION

Embodiments disclosed herein can reduce local muscular activity and thereby reduce the appearance of cosmetic imperfections or irregularities, for example facial lines. In embodiments the cosmetic irregularities can comprise glabellar lines, forehead lines, "bunny" lines, smile irregularities, chin irregularities, platysmal bands, "marionette" lines, lip lines, crow's feet, eyebrow irregularities, combinations thereof, and the like.

Embodiments comprise methods comprising dermatological surgical procedures, such as treatment for Actinic Keratosis, Seborrheic Keratosis, Basocelular Carcinoma, Squamous Cell Carcinoma, and other lesions or subdermal cysts.

Figure 1:
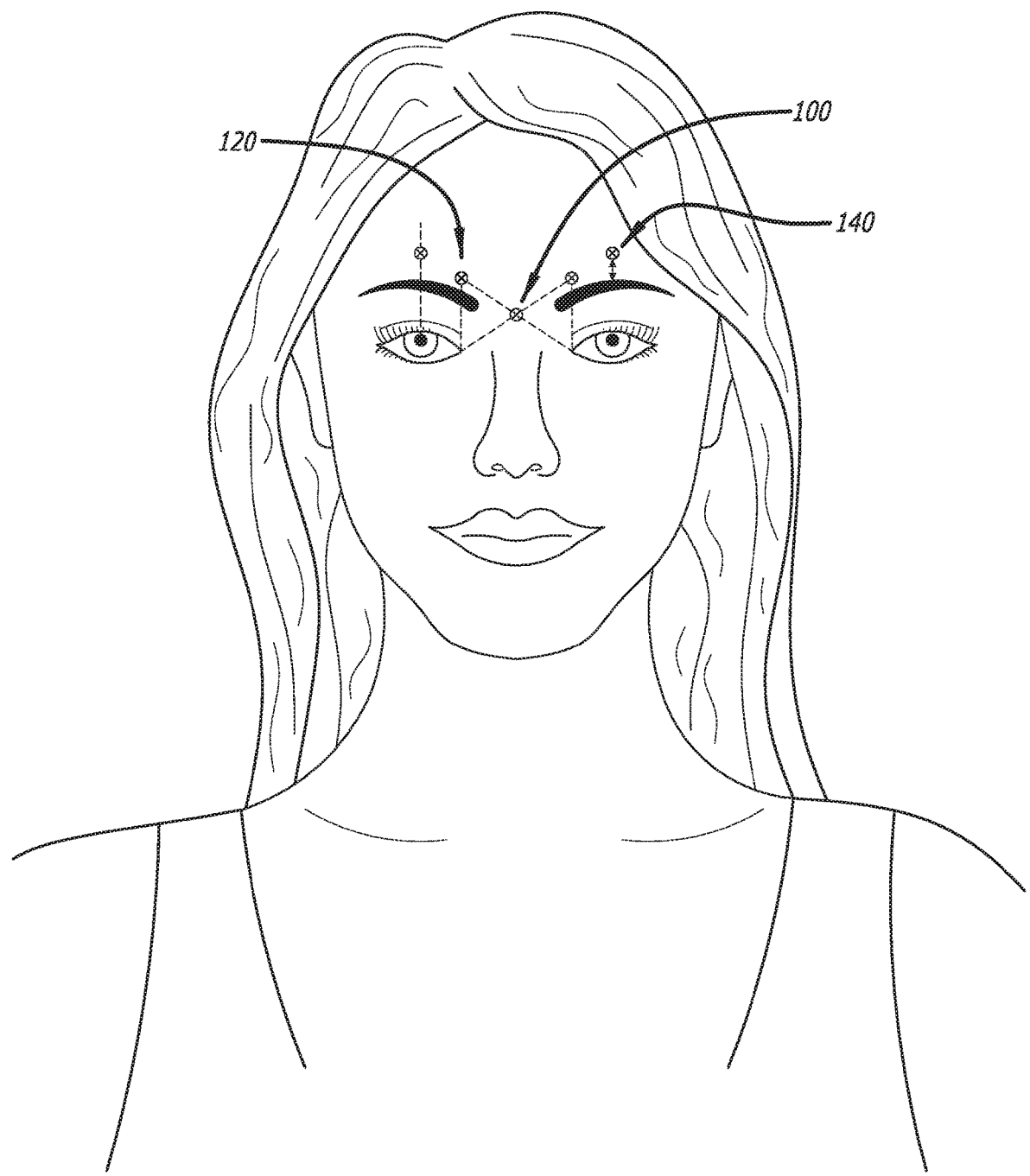
FIG. 1 depicts injection sites used in a cosmetic surgery procedure.

Administration sites useful for practicing the disclosed embodiments can comprise the glabellar complex, including the corrugator supercilli and the procerus; the obicularis oculi; the superolateral fibers of the obicularis oculi; the frontalis; the nasalis; the levator labii superioris aleque nasi; the obicularis oris; the masseter; the depressor anguli oris; and the platysma. Exemplary injection sites useful in glabellar line treatments are shown in FIG. 1.

Embodiments comprise treatment of gross wrinkles.

Disclosed embodiments can comprise treatment of, for example, skin disorders, for example, acne, and the like. Disclosed embodiments can comprise treatment of inflammatory skin diseases. For example, disclosed embodiments can comprise treatment of psoriasis, eczema, and the like.

Embodiments disclosed herein can reduce local muscular activity and thereby reduce the development of scars, for example scars resulting from surgery. In embodiments the surgery can comprise cosmetic surgery, for example rhinoplasty, an eye lift, a "tummy" tuck, or the like. In embodiments the surgery can comprise other types of medical procedures, for example appendix removal, organ transplant, and the like. In embodiments, methods comprise administering disclosed compositions in proximity to a wound.

Embodiments disclosed herein can reduce local muscular activity and thereby reduce the development of scars, for example scars resulting from trauma. For example, following a traumatic injury, disclosed embodiments can comprise administering disclosed compositions in proximity to trauma, for example a laceration or amputation.

Administration sites useful for practicing disclosed embodiments can comprise any area where muscle activity is to be reduced. For example, when employed in combination with facial cosmetic surgery procedures, disclosed embodiments can include administration to the glabellar complex, including the corrugator supercilli and the procerus; the obicularis oculi; the superolateral fibers of the obicularis oculi; the frontalis; the nasalis; the levator labii superioris aleque nasi; the obicularis oris; the masseter; the depressor anguli oris; and the platysma.

When employed in combination with other surgical procedures, disclosed embodiments can include administration to, for example, muscles of the arm, leg, torso, and the like.

Disclosed embodiments can comprise methods for preparing a surgical site prior to the procedure, in order to reduce muscle tension in the proximity of an incision.

Disclosed embodiments can promote the production of, for example, elastin, collagen, and the like. Disclosed embodiments can comprise methods of increasing the elasticity of the skin.

In embodiments, compositions disclosed herein can comprise fast-acting botulinum toxins, for example, type E.

In embodiments, compositions disclosed herein can comprise fast-recovery botulinum toxins, for example, type E.

In embodiments, compositions disclosed herein can comprise fast acting, fast-recovery botulinum toxins, for example, type E.

Definitions

"Administration," or "to administer" means the step of giving (i.e. administering) a pharmaceutical composition or active ingredient to a subject. The pharmaceutical compositions disclosed herein can be administered via a number of appropriate routs, however as described in the disclosed methods, the compositions are locally administered by e.g. intramuscular routes of administration, such as by injection or use of an implant.

"Botulinum toxin" or "botulinum neurotoxin" means a wild type neurotoxin derived from *Clostridium botulinum*, as well as modified, recombinant, hybrid and chimeric botulinum toxins. A recombinant botulinum toxin can have the light chain and/or the heavy chain thereof made recombinantly by a non-Clostridial species. "Botulinum toxin," as used herein, encompasses the botulinum toxin serotypes A, B, C, D, E, F, G and H. "Botulinum toxin," as used herein, also encompasses both a botulinum toxin complex (i.e. the 300, 600 and 900 kDa complexes) as well as pure botulinum toxin (i.e. the about 150 kDa neurotoxic molecule), all of which are useful in the practice of the present invention. "Purified botulinum toxin" means a pure botulinum toxin or a botulinum toxin complex that is isolated, or substantially isolated, from other proteins and impurities which can accompany the botulinum toxin as it is obtained from a culture or fermentation process. Thus, a purified botulinum toxin can have at least 95%, and more preferably at least 99% of the non-botulinum toxin proteins and impurities removed.

"Biocompatible" means that there is an insignificant inflammatory response at the site of implantation of an implant.

"Clostridial neurotoxin" means a neurotoxin produced from, or native to, a Clostridial bacterium, such as *Clostridium botulinum*, *Clostridium butyricum* or *Clostridium beratti*, as well as a Clostridial neurotoxin made recombinantly by a non-Clostridial species.

"Entirely free" ("consisting of" terminology) means that within the detection range of the instrument or process being used, the substance cannot be detected or its presence cannot be confirmed.

"Essentially free" means that within the detection range of the instrument or process being used, only trace amounts of the substance can be detected.

"Fast-acting" as used herein refers to a botulinum toxin that produces effects in the patient more rapidly than those produced by, for example, a botulinum neurotoxin type A. For example, the effects of a fast-acting botulinum toxin can be visible within 36 hours.

"Fast-recovery" as used herein refers to a botulinum toxin that whose effects diminish in the patient more rapidly than those produced by, for example, a botulinum neurotoxin type A. For example, the effects of a fast-recovery botulinum toxin can diminish within, for example, 120 hours, 150 hours, 300 hours, 350 hours, 400 hours, 500 hours, 600 hours, 700 hours, 800 hours, or the like. It is known that botulinum toxin type A can have an efficacy for up to 12 months. However, the usual duration of an intramuscular injection of a botulinum neurotoxin type A is typically about 3 to 4 months.

"Intermediate-acting" as used herein refers to a botulinum toxin that produces effects more slowly that a fast-acting toxin.

"Neurotoxin" means a biologically active molecule with a specific affinity for a neuronal cell surface receptor. Neurotoxin includes Clostridial toxins both as pure toxin and as complexed with one to more non-toxin, toxin associated proteins.

"Patient" means a human or non-human subject receiving medical or veterinary care.

"Pharmaceutical composition" means a formulation in which an active ingredient can be a botulinum toxin. The word "formulation" means that there is at least one additional ingredient (such as, for example and not limited to, an albumin [such as a human serum albumin or a recombinant human albumin] and/or sodium chloride) in the pharmaceutical composition in addition to a botulinum neurotoxin active ingredient. A pharmaceutical composition is therefore a formulation which is suitable for diagnostic, therapeutic or cosmetic administration to a subject, such as a human patient. The pharmaceutical composition can be: in a lyophilized or vacuum dried condition, a solution formed after reconstitution of the lyophilized or vacuum dried pharmaceutical composition with saline or water, for example, or; as a solution that does not require reconstitution. As stated, a pharmaceutical composition can be liquid or solid. A pharmaceutical composition can be animal-protein free.

"Substantially free" means present at a level of less than one percent by weight of a culture medium, fermentation medium, pharmaceutical composition or other material in which the weight percent of a substance is assessed.

"Supplemental administration" as used herein refers to a botulinum administration that follows an initial neurotoxin administration.

"Therapeutic formulation" means a formulation that can be used to treat and thereby alleviate a disorder or a disease and/or symptom associated thereof, such as a disorder or a disease characterized by an activity of a peripheral muscle.

"Therapeutically effective amount" means the level, amount or concentration of an agent (e.g. such as a botulinum toxin or pharmaceutical composition comprising botulinum toxin) needed to treat a disease, disorder or condition without causing significant negative or adverse side effects.

"Treat," "treating," or "treatment" means an alleviation or a reduction (which includes some reduction, a significant reduction a near total reduction, and a total reduction), resolution or prevention (temporarily or permanently) of an disease, disorder or condition, so as to achieve a desired therapeutic or cosmetic result, such as by healing of injured or damaged tissue, or by altering, changing, enhancing, improving, ameliorating and/or beautifying an existing or perceived disease, disorder or condition.

"Unit" or "U" means an amount of active BoNT standardized to have equivalent neuromuscular blocking effect as a Unit of commercially available botulinum neurotoxin type A.

Neurotoxin Compositions

Embodiments disclosed herein comprise neurotoxin compositions, for example fast-acting neurotoxin compositions, for example botulinum type E compositions. Such neurotoxins can be formulated in any pharmaceutically acceptable formulation in any pharmaceutically acceptable form. The neurotoxin can also be used in any pharmaceutically acceptable form supplied by any manufacturer.

Embodiments disclosed herein comprise neurotoxin compositions, for example fast-recovery neurotoxins. Such neurotoxins can be formulated in any pharmaceutically acceptable formulation in any pharmaceutically acceptable form. The neurotoxin can also be used in any pharmaceutically acceptable form supplied by any manufacturer.

Embodiments disclosed herein can comprise multiple neurotoxins. For example, in embodiments disclosed compositions can comprise two types of neurotoxins, for example two types of botulinum neurotoxins, such as a fast-acting and a slower-acting neurotoxin, for example type E and type A. In embodiments, disclosed compositions can comprise a fragment of a botulinum neurotoxin, for example, a 50 kDa light chain (LC).

The neurotoxin can be made by a Clostridial bacterium, such as by a *Clostridium botulinum, Clostridium butyricum,* or *Clostridium beratti* bacterium. Additionally, the neurotoxin can be a modified neurotoxin; that is a neurotoxin that has at least one of its amino acids deleted, modified or replaced, as compared to the native or wild type neurotoxin. Furthermore, the neurotoxin can be a recombinant produced neurotoxin or a derivative or fragment thereof.

In embodiments, a disclosed type E composition has 40% amino acid homology compared with type A and they share the same basic domain structure consisting of 2 chains, a 100 kDa heavy chain (HC) and a 50 kDa light chain (LC), linked by a disulfide bond (Whelan 1992). The HC contains the receptor binding domain and the translocation domain while the LC contains the synaptosomal-associated protein (SNAP) enzymatic activity. The domain structure is the same structure shared by all botulinum neurotoxin serotypes.

In disclosed embodiments, the neurotoxin is formulated in unit dosage form; for example, it can be provided as a sterile solution in a vial or as a vial or sachet containing a lyophilized powder for reconstituting a suitable vehicle such as saline for injection.

In embodiments, the botulinum toxin is formulated in a solution containing saline and pasteurized human serum albumin, which stabilizes the toxin and minimizes loss through non-specific adsorption. The solution can be sterile filtered (0.2µ filter), filled into individual vials and then vacuum-dried to give a sterile lyophilized powder. In use, the powder can be reconstituted by the addition of sterile unpreserved normal saline (sodium chloride 0.9% for injection).

In an embodiment, botulinum type E is supplied in a sterile solution for injection with a 5-mL vial nominal concentration of 20 ng/mL in 0.03 M sodium phosphate, 0.12 M sodium chloride, and 1 mg/mL Human Serum Albumin (HSA), at pH 6.0.

In an embodiment, botulinum type E is supplied in a sterile solution for injection with a 5-mL vial nominal concentration of 10 ng/mL in 0.03 M sodium phosphate, 0.12 M sodium chloride, and 1 mg/mL HSA, at pH 6.0.

In an embodiment, botulinum type E is supplied in a sterile solution for injection with a 5-mL vial nominal concentration of 5 ng/mL in 0.03 M sodium phosphate, 0.12 M sodium chloride, and 1 mg/mL HSA, at pH 6.0.

In an embodiment, botulinum type E is supplied in a sterile solution for injection with a 5-mL vial nominal concentration of 1 ng/mL in 0.03 M sodium phosphate, 0.12 M sodium chloride, and 1 mg/mL HSA, at pH 6.0.

Although the composition may only contain a single type of neurotoxin, such as botulinum type E, disclosed compositions can include two or more types of neurotoxins, which can provide enhanced therapeutic effects of the disorders. For example, a composition administered to a patient can include botulinum types A and E. Administering a single composition containing two different neurotoxins can permit the effective concentration of each of the neurotoxins to be lower than if a single neurotoxin is administered to the patient while still achieving the desired therapeutic effects. The composition administered to the patient can also contain other pharmaceutically active ingredients, such as, protein receptor or ion channel modulators, in combination with the neurotoxin or neurotoxins. These modulators may contribute to the reduction in neurotransmission between the various neurons. For example, a composition may contain gamma aminobutyric acid (GABA) type A receptor modulators that enhance the inhibitory effects mediated by the $GABA_A$ receptor. The $GABA_A$ receptor inhibits neuronal activity by effectively shunting current flow across the cell membrane. $GABA_A$ receptor modulators may enhance the inhibitory effects of the $GABA_A$ receptor and reduce electrical or chemical signal transmission from the neurons. Examples of $GABA_A$ receptor modulators include benzodiazepines, such as diazepam, oxaxepam, lorazepam, prazepam, alprazolam, halazeapam, chordiazepoxide, and chlorazepate. Compositions may also contain glutamate receptor modulators that decrease the excitatory effects mediated by glutamate receptors. Examples of glutamate receptor modulators include agents that inhibit current flux through AMPA, NMDA, and/or kainate types of glutamate receptors. The compositions may also include agents that modulate dopamine receptors, such as antipsychotics, norepinephrine receptors, and/or serotonin receptors. The compositions may also include agents that affect ion flux through voltage gated calcium channels, potassium channels, and/or sodium channels. Thus, the compositions used in disclosed embodiments may include one or more neurotoxins, such as botulinum toxins, in addition to ion channel receptor modulators that may reduce neurotransmission.

Methods of Use

Methods disclosed herein can comprise administration of a fast-acting neurotoxin to a patient. In a preferred embodiment the neurotoxin is botulinum type E.

Methods disclosed herein can comprise administration of a fast-recovery neurotoxin to a patient. In a preferred embodiment the neurotoxin is botulinum type E.

Before administering compositions disclosed herein, careful consideration is given to the anatomy of the treatment site. For example, in embodiments, the therapeutic goal is to inject the area with the highest concentration of neuromuscular junctions, if known. For example, in the case of intramuscular administration, before injecting the muscle the position of the needle in the muscle can be confirmed by putting the muscle through its range of motion and observing the resultant motion of the needle end. General anesthesia, local anesthesia and sedation are used according to the age of the patient, the number of sites to be injected, and the particular needs of the patient. More than one injection and/or sites of injection may be necessary to achieve the desired result. Also, some injections, depending on the muscle to be injected, may require the use of fine, hollow, TEFLON®-coated needles, guided by electromyography.

Administration of disclosed compositions can comprise, for example, injection, into or in the vicinity of one or more of the following skeletal muscles, for example, the occipitofrontalis, nasalis, orbicularis oris, depressor anguli oris, platysma, sternohyoid, serratus anterior, rectus abdominis, external oblique, tensor fasciae latae, brachioradialis, Iliacus, psoas major, pectineus, adductor longus, sartorius, gracillis, vastus lateralis, rectus femoris, vastus medialis, tendon of quadriceps femoris, patella, gastroctnemius, soleus, tibia, fibularis longus, tibialis anterior, patellar ligament, iliotibial tract, hypothenar muscles, thenar muscles, flexor carpi ulnaris, flexor digitorum superficialis, palmaris longus, flexor carpi radials, brachioradialis, pronator teres, brachialis, biceps brachii, triceps brachii, pectoralis major, deltoid, trapezius, sternocleidomastoid, masseter, orbicularis oculi, temporalis, epicranial aponeurosis, teres major, extensor digitorum, extensor carpi ulnaris, anconeus, abductor policis longus, plantaris, calcanel tendon, soleus, adductor magnus, gluteus maximas, gluteus medius, latissimus dorsi, intraspinatus, and combinations thereof, and the like.

Administration of disclosed compositions can comprise, for example, injection into or in the vicinity of one or more of the following nerves, for example, the axillary nerve, phrenic nerve, spinal ganglion, spinal cord, sypathetic ganglia chain, pudendal nerve, common palmar digital nerve, ulnar nerve, deep branch of the ulnar nerve, sciatic nerve, peroneal nerve, tibial nerve, saphenous nerve, interosseous nerve, superficial peroneal nerve, intermediate dorsal cutaneous nerve, medial plantar nerve, medial dorsal cutaneous nerve, deep peroneal nerve, muscular branches of tibial nerve, intrapatellar branch of saphenous nerve, common peroneal nerve, muscular branch of femoral nerve, anterior cutaneous branches of femoral nerve, muscular branches of sciatic nerve, femoral nerve, ilioinguinal, filum terminate, iliohypogastric, obturator, ulnar, radial, obturator, radial, subcostal, intercostal, dorsal branches of the intercostal, medial cutaneous branches of the intercostal, musculaneous, deltoid, vagus, brachial plexus, supraclavicular, facial, auriculotemporal, combinations thereof, and the like.

Smooth muscles suitable for administration of disclosed compositions can comprise any of walls of blood vessels, walls of stomach, ureters, intestines, in the aorta (tunica media layer), iris of the eye, prostate, gastrointestinal tract, respiratory tract, small arteries, arterioles, reproductive tracts (both genders), veins, glomeruli of the kidneys (called mesangial cells), bladder, uterus, arrector pili of the skin, ciliary muscle, sphincter, trachea, bile ducts, and the like.

The frequency and the amount of injection under the disclosed methods can be determined based on the nature and location of the particular area being treated. In certain cases, however, repeated or supplemental injection may be desired to achieve optimal results. The frequency and the amount of the injection for each particular case can be determined by the person of ordinary skill in the art.

In embodiments, administration of the fast acting neurotoxin is performed prior to a surgical procedure. In embodiments, the administration is performed, for example, within 36 hours before the procedure, within 24 hours before the procedure, within 22 hours before the procedure, within 20 hours before the procedure, within 18 hours before the procedure, within 16 hours before the procedure, within 14 hours before the procedure, within 12 hours before the procedure, within 11 hours before the procedure, within 10 hours before the procedure, within 9 hours before the procedure, within 8 hours before the procedure, within 7 hours before the procedure, within 6 hours before the procedure, within 5 hours before the procedure, within 4 hours before the procedure, within 3 hours before the procedure, within 2 hours before the procedure, within 60 minutes before the procedure, within 50 minutes before the procedure, within 40 minutes before the procedure, within 30 minutes before the procedure, within 20 minutes before the procedure, within 10 minutes before the procedure, within 5 minutes before the procedure, within 2 minutes before the procedure, or the like.

In embodiments, administration of the fast acting neurotoxin is performed prior to a surgical procedure. In embodiments, the administration is performed, for example, not less than 36 hours before the procedure, not less than 24 hours before the procedure, not less than 22 hours before the procedure, not less than 20 hours before the procedure, not less than 18 hours before the procedure, not less than 16 hours before the procedure, not less than 14 hours before the procedure, not less than 12 hours before the procedure, not less than 11 hours before the procedure, not less than 10 hours before the procedure, not less than 9 hours before the procedure, not less than 8 hours before the procedure, not less than 7 hours before the procedure, not less than 6 hours before the procedure, not less than 5 hours before the procedure, not less than 4 hours before the procedure, not less than 3 hours before the procedure, not less than 2 hours before the procedure, not less than 60 minutes before the procedure, not less than 50 minutes before the procedure, not less than 40 minutes before the procedure, not less than 30 minutes before the procedure, not less than 20 minutes before the procedure, not less than 10 minutes before the procedure, not less than 5 minutes before the procedure, not less than 2 minutes before the procedure, or the like.

In embodiments, administration of the fast acting neurotoxin is performed concurrently with a surgical procedure.

In embodiments, administration of the fast acting neurotoxin is performed after a surgical procedure. For example, administration can be performed, within 1 minute after the procedure, within 2 minutes after the procedure, within 3 minutes after the procedure, within 4 minutes after the procedure, within 5 minutes after the procedure, within 6 minutes after the procedure, within 7 minutes after the procedure, within 8 minutes after the procedure, within 9 minutes after the procedure, within 10 minutes after the procedure, within 20 minutes after the procedure, within 30 minutes after the procedure, within 40 minutes after the procedure, within 50 minutes after the procedure, within 60 minutes after the procedure, within 90 minutes after the procedure, within 2 hours after the procedure, within 3 hours after the procedure, within 4 hours after the procedure, within 5 hours after the procedure, within 6 hours after the procedure, within 7 hours after the procedure, within 8 hours after the procedure, within 9 hours after the procedure, within 10 hours after the procedure, within 11 hours after the procedure, within 12 hours after the procedure, or the like.

Methods disclosed herein can comprise supplemental administration of a fast-acting neurotoxin to a patient after an initial administration. Embodiments comprising supplemental administration can further comprise doctor or patient evaluation of the results of a prior neurotoxin administration. Such evaluation can comprise the use of, for example, photographs, scanning, or the like.

In embodiments, evaluation of the results of the initial neurotoxin administration can be performed within, for example, 6 hours of the initial administration, 8 hours of the initial administration, 10 hours of the initial administration, 12 hours of the initial administration, 14 hours of the initial administration, 16 hours of the initial administration, 18 hours of the initial administration, 24 hours of the initial administration, 30 hours of the initial administration, 36 hours of the initial administration, 42 hours of the initial administration, 48 hours of the initial administration, 54 hours of the initial administration, 60 hours of the initial administration, 66 hours of the initial administration, 72 hours of the initial administration, 78 hours of the initial administration, 84 hours of the initial administration, 90 hours of the initial administration, 96 hours of the initial administration, 102 hours of the initial administration, 108 hours of the initial administration, 114 hours of the initial administration, 120 hours of the initial administration, 1 week of the initial administration, 2 weeks of the initial administration, 3 weeks of the initial administration, 4 weeks of the initial administration, 5 weeks of the initial administration, 6 weeks of the initial administration, 7 weeks of the initial administration, 8 weeks of the initial administration, 9 weeks of the initial administration, 10 weeks of the initial administration, 11 weeks of the initial administration, 12 weeks of the initial administration, or the like.

In embodiments comprising a supplemental administration, administration of the supplemental dose can be performed, within, for example, 6 hours of the evaluation, 8 hours of the evaluation, 10 hours of the evaluation, 12 hours of the evaluation, 14 hours of the evaluation, 16 hours of the evaluation, 18 hours of the evaluation, 24 hours of the evaluation, 30 hours of the evaluation, 36 hours of the evaluation, 42 hours of the evaluation, 48 hours of the evaluation, 54 hours of the evaluation, 60 hours of the evaluation, 66 hours of the evaluation, 72 hours of the evaluation, 78 hours of the evaluation, 84 hours of the evaluation, 90 hours of the evaluation, 96 hours of the evaluation, 102 hours of the evaluation, 108 hours of the evaluation, 114 hours of the evaluation, 120 hours of the evaluation, 1 week of the evaluation, 2 weeks of the evaluation, 3 weeks of the evaluation, 4 weeks of the evaluation, 5 weeks of the evaluation, 6 weeks of the evaluation, 7 weeks of the evaluation, 8 weeks of the evaluation, 9 weeks of the evaluation, 10 weeks of the evaluation, 11 weeks of the evaluation, 12 weeks of the evaluation, or the like.

In embodiments, the supplemental administration can be performed, for example, within, for example, 6 hours of the initial administration, 8 hours of the initial administration, 10 hours of the initial administration, 12 hours of the initial administration, 14 hours of the initial administration, 16 hours of the initial administration, 18 hours of the initial administration, 24 hours of the initial administration, 30 hours of the initial administration, 36 hours of the initial administration, 42 hours of the initial administration, 48 hours of the initial administration, 54 hours of the initial administration, 60 hours of the initial administration, 66 hours of the initial administration, 72 hours of the initial administration, 78 hours of the initial administration, 84 hours of the initial administration, 90 hours of the initial administration, 96 hours of the initial administration, 102 hours of the initial administration, 108 hours of the initial administration, 114 hours of the initial administration, 120 hours of the initial administration, 1 week of the initial administration, 2 weeks of the initial administration, 3 weeks of the initial administration, 4 weeks of the initial administration, 5 weeks of the initial administration, 6 weeks of the initial administration, 7 weeks of the initial administration, 8 weeks of the initial administration, 9 weeks of the initial administration, 10 weeks of the initial administration, 11 weeks of the initial administration, 12 weeks of the initial administration, or the like.

Methods disclosed herein can provide rapid-onset effects (for example, using a fast-acting neurotoxin). For example, disclosed embodiments can provide visible cosmetic effect within, for example, 30 minutes after administration, 45 minutes after administration, 60 minutes after administration, 75 minutes after administration, 90 minutes after administration, 2 hours after administration, 3 hours after administration, 4 hours after administration, 5 hours after administration, 6 hours after administration, 7 hours after administration, 8 hours after administration, 9 hours after administration, 10 hours after administration, 11 hours after administration, 12 hours after administration, 13 hours after administration, 14 hours after administration, 15 hours after administration, 16 hours after administration, 17 hours after administration, 18 hours after administration, 19 hours after administration, 20 hours after administration, 21 hours after administration, 22 hours after administration, 23 hours after administration, 24 hours after administration, 30 hours after administration, 36 hours after administration, 42 hours after administration, 48 hours after administration, 3 days after administration, 4 days after administration, 5 days after administration, 6 days after administration, 7 days after administration, 8 days after administration, 9 days after administration, 10 days after administration, 11 days after administration, 12 days after administration, or the like.

Methods disclosed herein can provide effects of a shorter direction (for example, using a fast-recovery neurotoxin). For example, disclosed embodiments can provide visible cosmetic effect that subside within, for example, 3 days after administration, 4 days after administration, 5 days after administration, 6 days after administration, 7 days after administration, 8 days after administration, 9 days after administration, 10 days after administration, 11 days after administration, 12 days after administration, 13 days after administration, 14 days after administration, 15 days after administration, 16 days after administration, 17 days after administration, 18 days after administration, 19 days after administration, 20 days after administration, 21 days after administration, 22 days after administration, 23 days after administration, 24 days after administration, 25 days after administration, 26 days after administration, 27 days after administration, 28 days after administration, 29 days after administration, 30 days after administration, 45 days after administration, 60 days after administration, 75 days after administration, 90 days after administration, 105 days after administration, or the like.

Side-effects can be associated with botulinum injections. Disclosed embodiments can provide neurotoxin treatments that result in fewer side effects, or side effects of a shorted duration, than conventional neurotoxin treatments.

For example, disclosed embodiments can result in fewer (or shorter duration) instances of double vision or blurred vision, eyelid paralysis (subject cannot lift eyelid all the way open), loss of facial muscle movement, hoarseness, loss of bladder control, shortness of breath, difficulty in swallowing, difficulty speaking, death, and the like.

The present methods are particularly suitable for treatment of cosmetic irregularities, which are usually results of aging, environmental exposure, weight loss, child bearing, injury, surgery, or combinations thereof. Aging and environmental exposure often cause wrinkles on various positions of the skin. Weight loss and child bearing, on the other hand, often cause stretch marks on various positions of the skin, especially on stomach, areas of the lower body, and legs. Injury and surgery often result in scars in areas of injury and operation. Specific contour deficiencies suitable for treatment by the disclosed methods include, but are not limited to, frown lines, worry lines, wrinkles, crow's feet, marionette lines, stretch marks, wounds, accidents, bites, surgery, or the like. Particularly suitable for treatment according to the present invention are contour deficiencies of such areas as eyes, cheeks, nose, lips, forehead, and neck.

Further, disclosed embodiments can provide patients with cosmetic results of a more-certain duration. For example, with a longer acting neurotoxin, a 20% variance in duration of effects can result in a month's difference in effective duration. With the disclosed fast-recovery neurotoxins, this 20% variance produces a much less drastic difference in effective duration.

Supplemental administrations of a fast-acting neurotoxin can effectively modify or augment previous cosmetic neurotoxin administrations. For example, methods disclosed herein can comprise a supplemental administration to correct an uneven cosmetic result from a previous administration, or to increase the cosmetic effects of a previous administration, or to accelerate the onset of results as compared to those achieved using non fast-acting neurotoxins.

Disclosed fast-acting neurotoxin compositions can be administered using a needle or a needleless device. In certain embodiments, the method comprises subdermally injecting the composition in the individual. For example, administration may comprise injecting the composition through a needle no greater than about 30 gauge. In certain embodiments, the method comprises administering a composition comprising a botulinum toxin type E.

Injection of the compositions can be carried out by syringe, catheters, needles and other means for injecting. The injection can be performed on any area of the mammal's body that is in need of treatment, including, but not limited to, face, neck, torso, arms, hands, legs, and feet. The injection can be into any position in the specific area such as epidermis, dermis, fat, muscle, or subcutaneous layer.

The frequency and the amount of injection under the disclosed methods can be determined based on the nature and location of the particular cosmetic irregularity being treated. In certain cases, however, repeated injection may be desired to achieve optimal results. The frequency and the amount of the injection for each particular case can be determined by the person of ordinary skill in the art.

Although examples of routes of administration and dosages are provided, the appropriate route of administration and dosage are generally determined on a case by case basis by the attending physician. Such determinations are routine to one of ordinary skill in the art. For example, the route and dosage for administration of a Clostridial neurotoxin according to the present disclosed invention can be selected based upon criteria such as the solubility characteristics of the neurotoxin chosen as well as the intensity and scope of the cosmetic condition being treated.

The fast-acting neurotoxin can be administered in an amount of between about $10^{-3}$ U/kg and about 35 U/kg body weight. In an embodiment, the neurotoxin is administered in an amount of between about $10^{-2}$ U/kg and about 25 U/kg. In another embodiment, the neurotoxin is administered in an amount of between about $10^{-1}$ U/kg and about 15 U/kg. In another embodiment, the neurotoxin is administered in an amount of between about 1 U/kg and about 10 U/kg. In many instances, an administration of from about 1 unit to about 500 units of a neurotoxin, such as a botulinum type E, provides effective therapeutic relief. In an embodiment, from about 5 units to about 200 units of a neurotoxin, such as a botulinum type E, can be used and in another embodiment, from about 10 units to about 100 units of a neurotoxin, such as a botulinum type E, can be locally administered into a target tissue such as a muscle.

In embodiments, administration can comprise a dose of about 4 units of a neurotoxin, or about 5 units of a neurotoxin, or about 6 units of a neurotoxin, or about 7 units of a neurotoxin, or about 8 units of a neurotoxin, or about 10 units of a neurotoxin, or about 15 units of a neurotoxin, or about 20 units of a neurotoxin, or about 30 units of a neurotoxin, or about 40 units of a neurotoxin, or about 50 units of a neurotoxin, or about 60 units of a neurotoxin, or about 70 units of a neurotoxin, or about 80 units of a neurotoxin, or about 90 units of a neurotoxin, or about 100 units of a neurotoxin, or about 110 units of a neurotoxin, or about 120 units of a neurotoxin, or about 130 units of a neurotoxin, or about 140 units of a neurotoxin, or about 150 units of a neurotoxin, or about 160 units of a neurotoxin, or about 170 units of a neurotoxin, or about 180 units of a neurotoxin, or about 190 units of a neurotoxin, or about 200 units of a neurotoxin, or about 210 units of a neurotoxin, or about 220 units of a neurotoxin, or about 230 units of a neurotoxin, or about 240 units of a neurotoxin, or about 250 units of a neurotoxin, or about 260 units of a neurotoxin, or about 270 units of a neurotoxin, or about 280 units of a neurotoxin, or about 290 units of a neurotoxin, or about 290 units of a neurotoxin, or about 300 units of a neurotoxin, or about 310 units of a neurotoxin, or about 320 units of a neurotoxin, or about 330 units of a neurotoxin, or about 340 units of a neurotoxin, or about 350 units of a neurotoxin, or about 360 units of a neurotoxin, or about 370 units of a neurotoxin, or about 380 units of a neurotoxin, or about 390 units of a neurotoxin, or about 400 units of a neurotoxin, or about 410 units of a neurotoxin, or about 420 units of a neurotoxin, or about 430 units of a neurotoxin, or about 440 units of a neurotoxin, or about 450 units of a neurotoxin, or about 460 units of a neurotoxin, or about 470 units of a neurotoxin, or about 480 units of a neurotoxin, or about 490 units of a neurotoxin, or about 500 units of a neurotoxin, or the like.

In embodiments, administration can comprise a dose of about 4 units of a botulinum type E neurotoxin, or about 5 units of a botulinum type E neurotoxin, or about 6 units of a botulinum type E neurotoxin, or about 7 units of a botulinum type E neurotoxin, or about 8 units of a botulinum type E neurotoxin, or about 10 units of a botulinum type E neurotoxin, or about 15 units of a botulinum type E neurotoxin, or about 20 units of a botulinum type E neurotoxin, or about 30 units of a botulinum type E neurotoxin, or about 40 units of a botulinum type E neurotoxin, or about 50 units of a botulinum type E neurotoxin, or about 60 units of a botulinum type E neurotoxin, or about 70 units of a botulinum type E neurotoxin, or about 80 units of a botulinum type E neurotoxin, or about 90 units of a botulinum type E neurotoxin, or about 100 units of a botulinum type E neurotoxin, or about 110 units of a botulinum type E neurotoxin, or about 120 units of a botulinum type E neurotoxin, or about 130 units of a botulinum type E neurotoxin, or about 140 units of a botulinum type E neurotoxin, or about 150 units of a botulinum type E neurotoxin, or about 160 units of a botulinum type E neurotoxin, or about 170 units of a botulinum type E neurotoxin, or about 180 units of a botulinum type E neurotoxin, or about 190 units of a botulinum type E neurotoxin, or about 200 units of a botulinum type E neurotoxin, or about 210 units of a botulinum type E neurotoxin, or about 220 units of a botulinum type E neurotoxin, or about 230 units of a botulinum type E neurotoxin, or about 240 units of a botulinum type E neurotoxin, or about 250 units of a botulinum type E neurotoxin, or about 260 units of a botulinum type E neurotoxin, or about 270 units of a botulinum type E neurotoxin, or about 280 units of a botulinum type E neurotoxin, or about 290 units of a botulinum type E neurotoxin, or about 290 units of a botulinum type E neurotoxin, or about 300 units of a botulinum type E neurotoxin, or about 310 units of a botulinum type E neurotoxin, or about 320 units of a botulinum type E neurotoxin, or about 330 units of a botulinum type E neurotoxin, or about 340 units of a botulinum type E neurotoxin, or about 350 units of a neurotoxin, or about 360 units of a botulinum type E neurotoxin, or about 370 units of a botulinum type E neurotoxin, or about 380 units of a botulinum type E neurotoxin, or about 390 units of a botulinum type E neurotoxin, or about 400 units of a botulinum type E neurotoxin, or about 410 units of a botulinum type E neurotoxin, or about 420 units of a botulinum type E neurotoxin, or about 430 units of a botulinum type E neurotoxin, or about 440 units of a botulinum type E neurotoxin, or about 450 units of a botulinum type E neurotoxin, or about 460 units of a botulinum type E neurotoxin, or about 470 units of a botulinum type E neurotoxin, or about 480 units of a botulinum type E neurotoxin, or about 490 units of a botulinum type E neurotoxin, or about 500 units of a botulinum type E neurotoxin, or the like.

Disclosed herein are methods for expressing neurotoxin dosages and conveying neurotoxin dosage amounts. In embodiments, the dosage amount is expressed in protein amount, for example nanograms (ng). In embodiments, the neurotoxin can comprise a botulinum toxin.

Methods disclosed herein can comprise administration of a neurotoxin, for example a fast-acting neurotoxin, to a patient, wherein the dosage of the neurotoxin is expressed in protein amount, for example protein amount per administration. In an embodiment the fast-acting neurotoxin is a botulinum toxin, for example botulinum type E.

In embodiments, the dose of the neurotoxin is expressed in protein amount or concentration. For example, in embodiments the neurotoxin can be administered in an amount of between about 0.2 ng and 20 ng. In an embodiment, the neurotoxin is administered in an amount of between about 0.3 ng and 19 ng, about 0.4 ng and 18 ng, about 0.5 ng and 17 ng, about 0.6 ng and 16 ng, about 0.7 ng and 15 ng, about 0.8 ng and 14 ng, about 0.9 ng and 13 ng, about 1.0 ng and 12 ng, about 1.5 ng and 11 ng, about 2 ng and 10 ng, about 5 ng and 7 ng, and the like into a target tissue such as a muscle.

In embodiments, administration can comprise a total dose of between 5 and 7 ng, between 7 and 9 ng, between 9 and 11 ng, between 11 and 13 ng, between 13 and 15 ng, between 15 and 17 ng, between 17 and 19 ng, or the like.

In embodiments, administration can comprise a total dose of not more than 5 ng, not more than 6 ng, not more than 7 ng, not more than 8 ng, not more than 9 ng, not more than 10 ng, not more than 11 ng, not more than 12 ng, not more than 13 ng, not more than 14 ng, not more than 15 ng, not more than 16 ng, not more than 17 ng, not more than 18 ng, not more than 19 ng, not more than 20 ng, or the like.

In embodiments, administration can comprise a total dose of not less than 5 ng, not less than 6 ng, not less than 7 ng, not less than 8 ng, not less than 9 ng, not less than 10 ng, not less than 11 ng, not less than 12 ng, not less than 13 ng, not less than 14 ng, not less than 15 ng, not less than 16 ng, not less than 17 ng, not less than 18 ng, not less than 19 ng, not less than 20 ng, or the like.

In embodiments, administration can comprise a total dose of about 0.1 ng of a neurotoxin, 0.2 ng of a neurotoxin, 0.3 ng of a neurotoxin, 0.4 ng of a neurotoxin, 0.5 ng of a neurotoxin, 0.6 ng of a neurotoxin, 0.7 ng of a neurotoxin, 0.8 ng of a neurotoxin, 0.9 ng of a neurotoxin, 1.0 ng of a neurotoxin, 1.1 ng of a neurotoxin, 1.2 ng of a neurotoxin, 1.3 ng of a neurotoxin, 1.4 ng of a neurotoxin, 1.5 ng of a neurotoxin, 1.6 ng of a neurotoxin, 1.7 ng of a neurotoxin, 1.8 ng of a neurotoxin, 1.9 ng of a neurotoxin, 2.0 ng of a neurotoxin, 2.1 ng of a neurotoxin, 2.2 ng of a neurotoxin, 2.3 ng of a neurotoxin, 2.4 ng of a neurotoxin, 2.5 ng of a neurotoxin, 2.6 ng of a neurotoxin, 2.7 ng of a neurotoxin, 2.8 ng of a neurotoxin, 2.9 ng of a neurotoxin, 3.0 ng of a neurotoxin, 3.1 ng of a neurotoxin, 3.2 ng of a neurotoxin, 3.3 ng of a neurotoxin, 3.4 ng of a neurotoxin, 3.5 ng of a neurotoxin, 3.6 ng of a neurotoxin, 3.7 ng of a neurotoxin, 3.8 ng of a neurotoxin, 3.9 ng of a neurotoxin, 4.0 ng of a neurotoxin, 4.1 ng of a neurotoxin, 4.2 ng of a neurotoxin, 4.3 ng of a neurotoxin, 4.4 ng of a neurotoxin, 4.5 ng of a neurotoxin, 5 ng of a neurotoxin, 6 ng of a neurotoxin, 7 ng of a neurotoxin, 8 ng of a neurotoxin, 9 ng of a neurotoxin, 10 ng of a neurotoxin, 11 ng of a neurotoxin, 12 ng of a neurotoxin, 13 ng of a neurotoxin, 14 ng of a neurotoxin, 15 ng of a neurotoxin, 16 ng of a neurotoxin, 17 ng of a neurotoxin, 18 ng of a neurotoxin, 19 ng of a neurotoxin, 20 ng of a neurotoxin, or the like.

In embodiments, administration can comprise a dose per injection of for example, about 0.1 ng of a botulinum type E neurotoxin, 0.2 ng of a botulinum type E neurotoxin, 0.3 ng of a botulinum type E neurotoxin, 0.4 ng of a botulinum type E neurotoxin, 0.5 ng of a botulinum type E neurotoxin, 0.6 ng of a botulinum type E neurotoxin, 0.7 ng of a botulinum type E neurotoxin, 0.8 ng of a botulinum type E neurotoxin, 0.9 ng of a botulinum type E neurotoxin, 1.0 ng of a botulinum type E neurotoxin, 1.1 ng of a botulinum type E neurotoxin, 1.2 ng of a botulinum type E neurotoxin, 1.3 ng of a botulinum type E neurotoxin, 1.4 ng of a botulinum type E neurotoxin, 1.5 ng of a botulinum type E neurotoxin, 1.6 ng of a botulinum type E neurotoxin, 1.7 ng of a botulinum type E neurotoxin, 1.8 ng of a botulinum type E neurotoxin, 1.9 ng of a botulinum type E neurotoxin, 2.0 ng of a botulinum type E neurotoxin, 2.1 ng of a botulinum type E neurotoxin, 2.2 ng of a botulinum type E neurotoxin, 2.3 ng of a botulinum type E neurotoxin, 2.4 ng of a neurotoxin, 2.5 ng of a neurotoxin, 2.6 ng of a botulinum type E neurotoxin, 2.7 ng of a botulinum type E neurotoxin, 2.8 ng of a botulinum type E neurotoxin, 2.9 ng of a botulinum type E neurotoxin, 3.0 ng of a botulinum type E neurotoxin, 3.1 ng of a botulinum type E neurotoxin, 3.2 ng of a botulinum type E neurotoxin, 3.3 ng of a botulinum type E neurotoxin, 3.4 ng of a botulinum type E neurotoxin, 3.5 ng of a botulinum type E neurotoxin, 3.6 ng of a botulinum type E neurotoxin, 3.7 ng of a botulinum type E neurotoxin, 3.8 ng of a botulinum type E neurotoxin, 3.9 ng of a botulinum type E neurotoxin, 4.0 ng of a botulinum type E neurotoxin, 4.1 ng of a botulinum type E neurotoxin, 4.2 ng of a botulinum type E neurotoxin, 4.3 ng of a botulinum type E neurotoxin, 4.4 ng of a botulinum type E neurotoxin, 4.5 ng of a botulinum type E neurotoxin, 5 ng of a botulinum type E neurotoxin, 6 ng of a botulinum type E neurotoxin, 7 ng of a botulinum type E neurotoxin, 8 ng of a botulinum type E neurotoxin, 9 ng of a botulinum type E neurotoxin, 10 ng of a botulinum type E neurotoxin, or the like.

Ultimately, however, both the quantity of toxin administered and the frequency of its administration will be at the discretion of the physician responsible for the treatment and will be commensurate with questions of safety and the effects produced by the toxin.

A controlled release system can be used in the embodiments described herein to deliver a neurotoxin in vivo at a predetermined rate over a specific time period. Generally, release rates are determined by the design of the system, and can be largely independent of environmental conditions such as pH. Controlled release systems which can deliver a drug over a period of several years are known. Contrarily, sustained release systems typically deliver drug in 24 hours or less and environmental factors can influence the release rate. Thus, the release rate of a neurotoxin from an implanted controlled release system (an "implant") is a function of the physiochemical properties of the carrier implant material and of the drug itself. Typically, the implant is made of an inert material which elicits little or no host response.

A controlled release system can be comprised of a neurotoxin incorporated into a carrier. The carrier can be a polymer or a bio-ceramic material. The controlled release system can be injected, inserted or implanted into a selected location of a patient's body and reside therein for a prolonged period during which the neurotoxin is released by the implant in a manner and at a concentration which provides a desired therapeutic efficacy.

Polymeric materials can release neurotoxins due to diffusion, chemical reaction or solvent activation, as well as upon influence by magnetic, ultrasound or temperature change factors. Diffusion can be from a reservoir or matrix. Chemical control can be due to polymer degradation or cleavage of the drug from the polymer. Solvent activation can involve swelling of the polymer or an osmotic effect.

Implants may be prepared by mixing a desired amount of a stabilized neurotoxin into a solution of a suitable polymer dissolved in methylene chloride. The solution may be prepared at room temperature. The solution can then be transferred to a Petri dish and the methylene chloride evaporated in a vacuum desiccator. Depending upon the implant size desired and hence the amount of incorporated neurotoxin, a suitable amount of the dried neurotoxin incorporating implant is compressed at about 8000 p.s.i. for 5 seconds or at 3000 p.s.i. for 17 seconds in a mold to form implant discs encapsulating the neurotoxin.

Preferably, the implant material used is substantially non-toxic, non-carcinogenic, and non-immunogenic. Suitable implant materials include polymers, such as poly(2-hydroxy ethyl methacrylate) (p-HEMA), poly(N-vinyl pyrrolidone) (p-NVP)+, poly(vinyl alcohol) (PVA), poly (acrylic acid) (PM), polydimethyl siloxanes (PDMS), ethylene-vinyl acetate (EVAc) copolymers, polyvinylpyrrolidone/methacrylate copolymers, polymethylmethacrylate (PMMA), poly(lactic acid) (PLA), poly(glycolic acid) (PGA), polyanhydrides, poly(ortho esters), collagen and cellulosic derivatives and bioceramics, such as hydroxyapatite (HPA), tricalcium phosphate (TCP), and aliminocalcium phosphate (ALCAP). Lactic acid, glycolic acid and collagen can be used to make biodegradable implants.

An implant material can be biodegradable or bioerodible. An advantage of a bioerodible implant is that it does not need to be removed from the patient. A bioerodible implant can be based upon either a membrane or matrix release of the bioactive substance. Biodegradable microspheres prepared from PLA-PGA are known for subcutaneous or intramuscular administration.

A kit for practicing disclosed embodiments is also encompassed by the present disclosure. The kit can comprise a 30 gauge or smaller needle and a corresponding syringe. The kit also comprises a Clostridial neurotoxin composition, such as a botulinum type E toxin composition. The neurotoxin composition may be provided in the syringe. The composition is injectable through the needle. The kits are designed in various forms based the sizes of the syringe and the needles and the volume of the injectable composition contained therein, which in turn are based on the specific cosmetic deficiencies the kits are designed to treat.

EXAMPLES

The following non-limiting examples are provided for illustrative purposes only in order to facilitate a more complete understanding of representative embodiments. This example should not be construed to limit any of the embodiments described in the present specification.

Example 1

Use of Botulinum Toxin Type E to Treat Glabellar Lines (GL)

This first-in-human, randomized, double-blinded, placebo-controlled, ascending dose cohort study enrolled 42 subjects who received EB-001 (a botulinum type E composition disclosed herein) (N=35) or placebo (N=7). The efficacy primary outcome was the proportion of subjects with a 2-grade investigator-rated (IR-2) improvement in GL severity at maximum frown. Safety evaluations included adverse events (AEs), laboratory tests, and physical examinations. An IR-2 response was observed starting in the third cohort (EB-001), with increased rates observed at higher doses. Onset of clinical effect was within 24 hours, with a duration ranging between 14 and 30 days for the highest doses. AE incidence was low, with the most common being mild to moderate headache. There were no serious AEs or ptosis, and no clinically significant changes in other safety assessments.

In this clinical study in GL, EB-001 showed favorable safety and tolerability, and dose dependent efficacy with an 80% response rate at the highest dose. EB-001 maximum clinical effect was seen within 24 hours and lasted between 14 and 30 days. This differentiated EB-001 profile supports its development for aesthetic and therapeutic applications where fast onset and short duration of effect are desirable.

Botulinum neurotoxins, which inhibit the pre-synaptic release of acetylcholine, are among the most potent molecules in nature. When injected into muscles, Botulinum neurotoxins inhibit neuromuscular transmission and produce dose-dependent local muscle relaxation. Purified Botulinum neurotoxins, including serotypes A and B have been developed as injectable drugs and are widely used to treat a variety of neuromuscular conditions. Botulinum neurotoxin serotype E is a novel serotype that has not been developed for clinical use to date. Botulinum toxin type E has the fastest onset and the shortest duration of action of all the Botulinum neurotoxins. Type E has similar domain structure to type A, consisting of 2 protein chains, a 100 kDa heavy chain and a 50 kDa light chain linked by a disulfide bond.2 Type E inhibits neuromuscular transmission by cleaving the same presynaptic vesicular protein (synaptosomal associated protein 25) as type A, but at a different cleavage site. Two binding sites on motor axons mediate the high affinity recognition of nerve cells by Botulinum neurotoxins. Binding is mediated first by cell surface gangliosides and then by specific protein receptors. These receptors are found on motor axon terminals at the neuromuscular junction. Botulinum toxin types A and E have both been shown to bind the specific receptor synaptic vesicle protein 2, and only these two serotypes share this receptor. This was the first clinical study to evaluate the safety and efficacy of ascending doses of Botulinum toxin type E in subjects with GL.

This study was a first-in-human evaluation of the safety and efficacy of EB-001 and focused on the treatment of moderate to severe GL. EB-001 is a proprietary purified form of Botulinum toxin type E, formulated as a liquid for injection (Bonti, Inc., Newport Beach, Calif., USA). This was a randomized, double-blinded, placebo-controlled, ascending-dose cohort study conducted at 2 expert clinical centers (Steve Yoelin, MD Medical Associates, Newport Beach, Calif., USA; Center for Dermatology Clinical Research, Fremont, Calif., USA). This study was approved by an Institutional Review Board (Aspire Institutional Review Board, Santee, Calif., USA) and was conducted in accordance with the guidelines set by the Declaration of Helsinki. Written informed consent was received from all subjects prior to their participation.

A total of 42 healthy toxin-naïve male and female subjects, ages 18 to 60 years, were enrolled in the study. Each subject's participation was to last approximately 6 weeks. The main inclusion criteria were: the presence of bilaterally symmetrical GL of moderate to severe rating at maximum frown, sufficient visual acuity without the use of eyeglasses (contact lens use acceptable) to accurately assess their facial wrinkles, and the ability to conform with study requirements. The main criteria for exclusion were: any uncontrolled systemic disease or other medical condition, any medical condition that may have put the subject at increased risk with exposure to Botulinum neurotoxin (including diagnosed myasthenia gravis, Eaton-Lambert syndrome, amyotrophic lateral sclerosis, or any other condition that interfered with neuromuscular function), current or prior Botulinum neurotoxin treatment, known immunization or hypersensitivity to Botulinum neurotoxin, pre-specified dermatological procedures within 3 to 12 months of the study (non-ablative resurfacing, facial cosmetic procedures, topical/oral retinoid therapy, etc.), and prior periorbital surgery or treatment. Women were not enrolled if they were pregnant, lactating, or planning to become pregnant. Men with female partner(s) of childbearing potential were enrolled only if they agreed to use dual methods of contraception for 3 months following dosing.

At Screening, subject demographics, medical history, and prior and concomitant medications were recorded and an alcohol/drug screen was performed. Standardized facial photography was performed at Baseline prior to treatment, and at every follow-up visit through the end of the study, but the photographs were not used for efficacy evaluations.

Seven cohorts (6 subjects per cohort) were enrolled and received ascending doses of EB-001 or placebo in a 5:1 ratio. The maximum recommended starting dose (with a 10-fold safety factor) in this first-in-human study was developed based on the no observed adverse effect levels from a preclinical safety and toxicity study (unpublished data). From this, a base dose (Cohort 1) was calculated and determined to be sub-efficacious, and Cohorts 2 to 7 received 3, 9, 12, 16, 21, and 28 times the base dose, respectively. This represented sub-efficacious to maximum-efficacious doses of EB-001. The total dose was delivered at 5 injection sites in equal volumes (0.1 mL per site into the procerus, left and right medial corrugators, and left and right lateral corrugators) in a standardized fashion (see FIG. 1). The spacing of injections into the lateral corrugators was approximately 1 cm above the supraorbital ridge. EB-001 was supplied in a sterile solution for injection in a 5-mL vial. The placebo was supplied in identical vials without EB-001.

Each subject completed visits at Screening (Day −30 to −1), Baseline/Injection (Day 0), Days 1, 2, 7, 14, and 30 (end of study), and Day 42 (final safety follow-up).

Safety was evaluated by adverse events (AEs), laboratory testing, electrocardiograms (ECGs), physical examinations, vital signs (pulse rate, respiratory rate, and blood pressure), urine pregnancy tests (for women of childbearing potential), and focused neurologic examinations to evaluate for the potential spread of Botulinum neurotoxin. Treatment-emergent AEs (TEAEs) were defined as any AE that started or worsened in severity after exposure to study treatment. AEs and TEAEs were summarized by system organ class and preferred term using the Medical Dictionary for Regulatory Activities (MedDRA, version 19.0). Serious AEs (SAEs, or AEs that fulfilled regulatory criteria for medical seriousness), and discontinuation due to AEs were also evaluated. Severity of AEs was recorded as mild, moderate, severe, or life threatening. Before enrollment of each dosing cohort, a safety data review committee met to analyze all safety data from the previous cohort(s).

At Screening, Baseline, and Days 1, 2, 7, 14, and 30, the subject's GL were assessed at maximum frown and at rest using the Facial Wrinkle Scale (FWS). Evaluations were completed by the investigator and the subject. The FWS is a widely accepted measure used for the evaluation of facial line severity. In the present study, the 4-point scale indicating severity of GL was as follows: 0=none, 1=mild, 2=moderate, 3=severe. Subjects were considered as treatment responders if they achieved at least a 2-grade improvement (reduction) based on the investigator's FWS assessment (IR-2). The primary efficacy variable was the proportion of IR-2 responders at maximum frown at any post baseline visit through Day 30. An additional efficacy endpoint of interest was the proportion of responders achieving an investigator-assessed FWS grade of none or mild at Days 1, 2, 7, 14, or 30 (analyzed by visit).

Two analysis populations were pre-specified, a safety and an efficacy population. Subjects receiving placebo were pooled for all analyses. The safety population included all subjects who received study treatment and had at least 1 safety assessment thereafter. All TEAEs and SAEs were summarized by treatment group. All safety parameters, including laboratory testing, ECGs, physical exams, vital signs, urine pregnancy tests, and focused neurologic examinations, were reviewed and evaluated for clinical significance by the investigators. The efficacy population was the modified intent-to-treat (mITT) population, defined as all randomized subjects who received at least 1 dose of study treatment and had at least 1 post baseline efficacy assessment. Analyses of demographics and baseline characteristics were performed on the mITT population. Medical history was based on the safety population and coded using MedDRA and summarized by system organ class and preferred term. Prior and concomitant medications were based on the safety population and coded using the World Health Organization Anatomical Therapeutic Chemical classification index and summarized by drug class and treatment group. Efficacy analyses were performed using the mITT population. FWS grades were summarized by treatment and study day using frequency counts and rates of response (%). An analysis comparing the proportion of IR-2 responders in each EB-001 cohort versus placebo (pooled) was performed using Fisher's exact test with a 0.05 level of significance.

Of the 59 subjects who were screened for the study, 43 were enrolled into 1 of 7 cohorts. One subject did not receive treatment, and consequently 42 subjects were included in the mITT and safety populations (35 treated with EB-001 and 7 treated with placebo). Forty-one subjects completed the study, with 1 subject lost to follow-up. The demographic and baseline characteristics of the mITT population are displayed in Table 1. The mean (range) ages of subjects for the EB-001 (pooled) versus placebo (pooled) groups were 47.9 (22 to 60) and 50.4 (32 to 57) years, respectively. The majority of subjects were female (EB-001=91.4%; placebo=85.7%) and white (71.4% for both groups). The baseline mean (standard deviation [SD]) investigator-assessed GL at maximum frown were 2.6 (0.50) and 2.9 (0.38) for the EB-001 and placebo groups, respectively. The EB-001 and placebo groups were well balanced with no substantial between-group differences.

Figure 2:
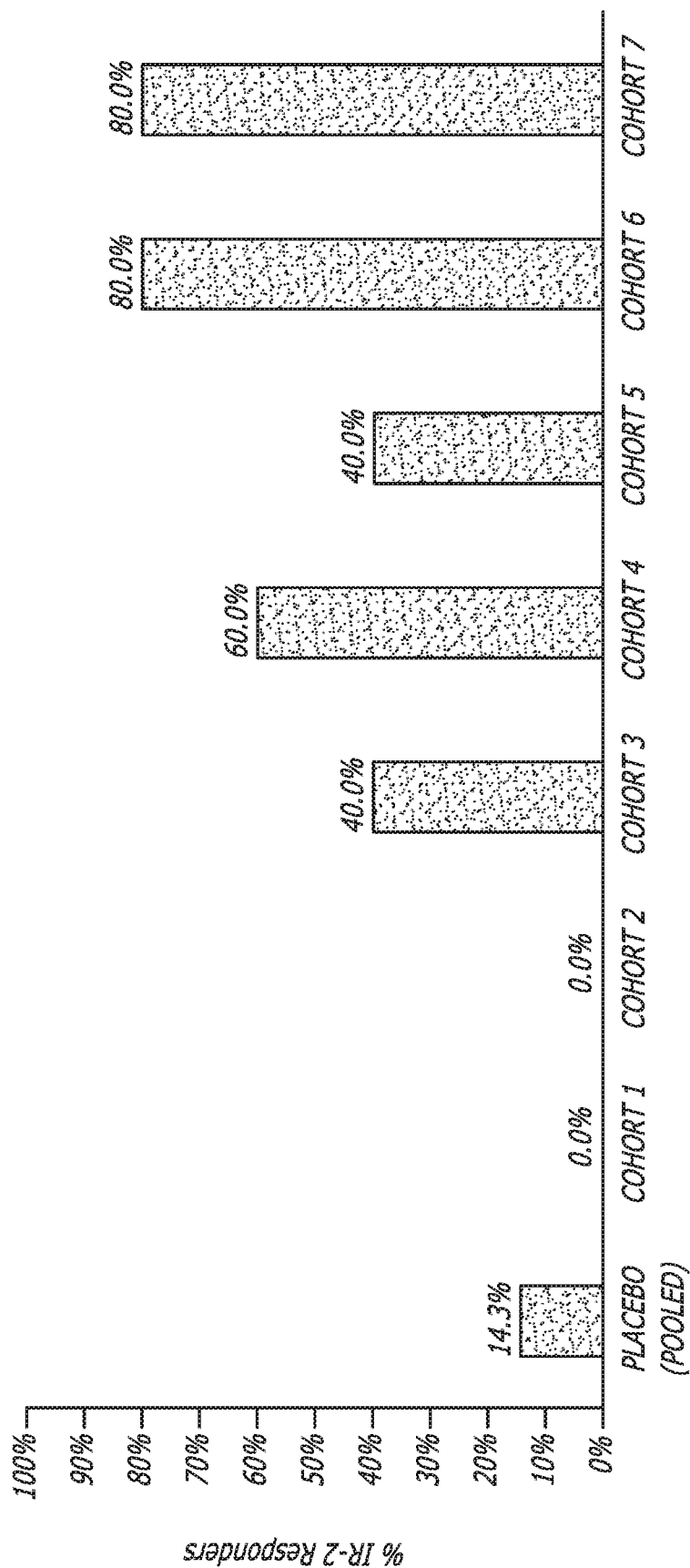
FIG. 2 shows primary efficacy of a glabellar line treatment study.
Figure 3:
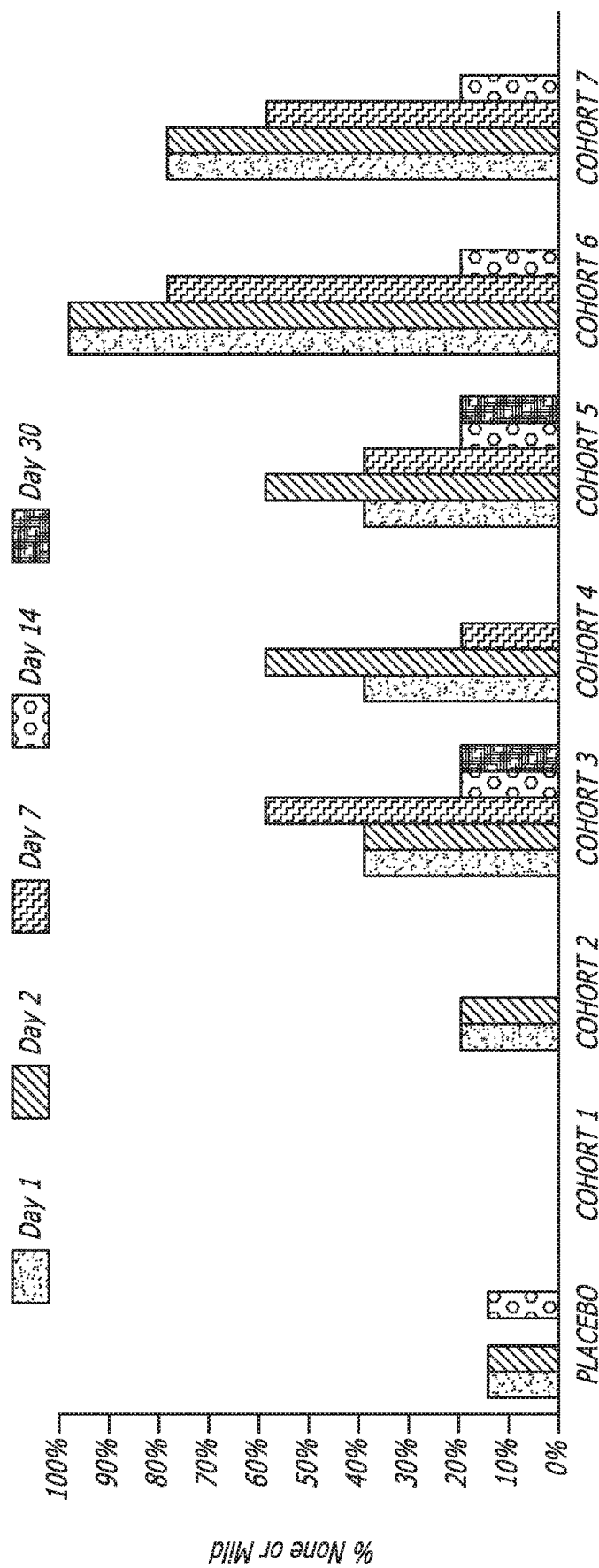
FIG. 3 shows secondary efficacy of a glabellar line treatment study.
Figure 4:
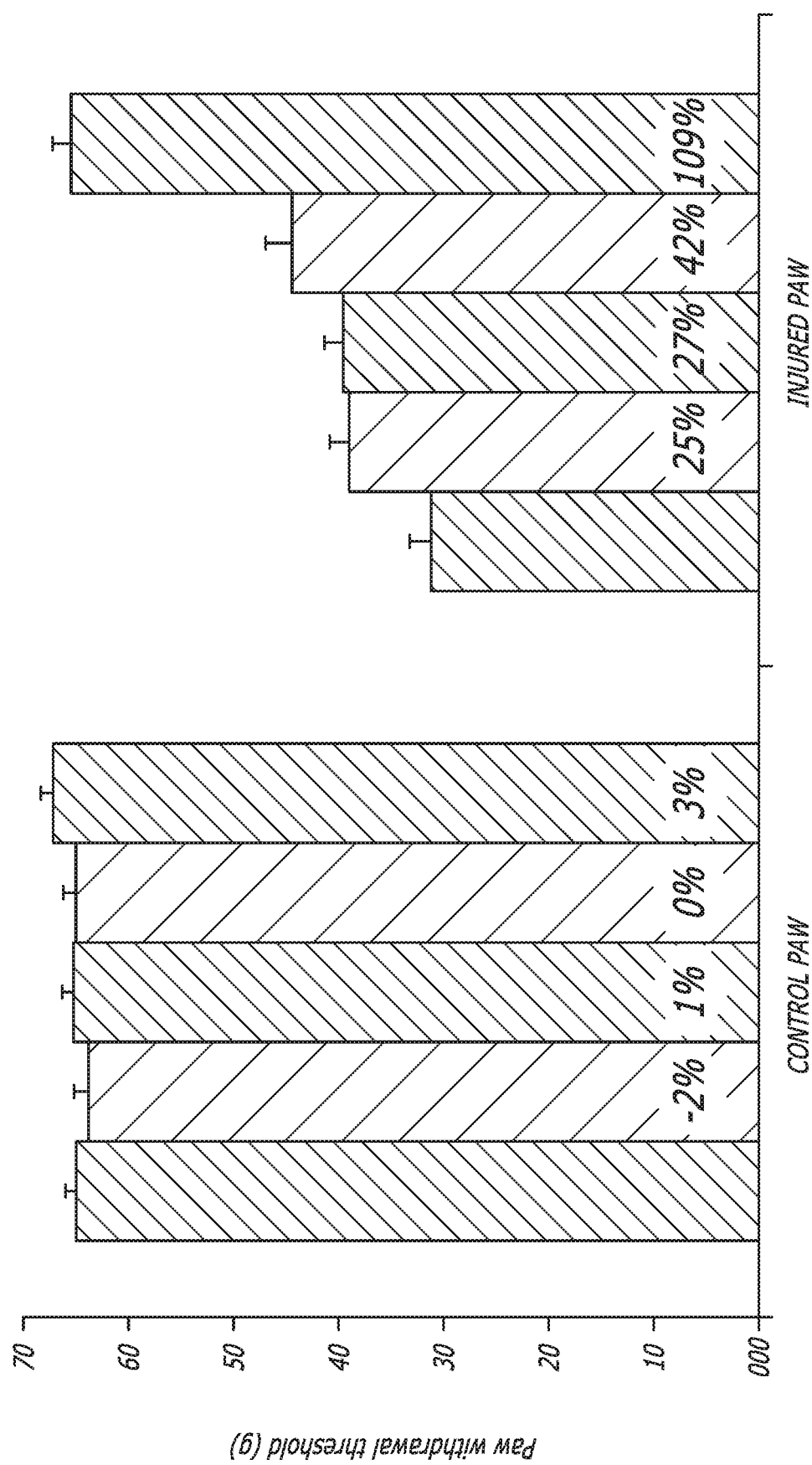
FIG. 4 shows the effect of a single local administration of a disclosed type E botulinum composition in a rat model of post-operative pain.

The proportions of subjects in the mITT population achieving an IR-2 response for GL severity at maximum frown at any postbaseline visit through Day 30 are presented by dose cohort in FIG. 2. In Cohort 3, 40% of subjects were IR-2 responders. This responder rate was the same or greater in all higher dose cohorts, with Cohorts 6 and 7 having 80% IR-2 responders. Cohorts 6 and 7 demonstrated significantly greater percentages of IR-2 responders versus placebo (P=0.046). FIG. 3 summarizes the proportions of subjects in each cohort with investigator-assessed FWS grades of none or mild GL at maximum frown, at any post baseline visit through Day 30. Cohorts 2 to 7 (inclusive) had greater percentages of responders versus placebo, with rates of 60% to 100% achieved for Cohorts 3 and higher. In Cohorts 3 to 7, most none or mild responses were observed at Days 1, 2, and/or 7. One responder (20%) was observed at Day 14 in Cohorts 3, 5, 6 and 7 and at Day 30 in Cohorts 3 and 5. The safety results support the safety of all evaluated doses of EB-001, administered as IM injections, in this population. No clinically significant changes from baseline in neurologic examinations, ECGs, physical examinations, or laboratory tests were observed for any subject.

Five subjects treated with EB-001 reported TEAEs, and none in placebo group. No SAEs were reported and no TEAE led to discontinuation of the study. All TEAEs were mild or moderate in severity. The events of sore throat and flu like symptoms were considered unrelated to treatment. Three subjects reported TEAEs of headache, 1 of which was considered related to treatment. There was no dose-related increase in the incidence of headaches. There were no events of ptosis or other TEAE possibly related to spread of toxin.

To our knowledge, this is the first controlled clinical trial of a Botulinum toxin type E product in any aesthetic or therapeutic use. This first-in-human study of EB-001, a novel purified form of Botulinum toxin type E administered IM, fulfilled its objectives of evaluating the safety, tolerability, and efficacious dose-range of EB-001. A dose response was observed, with greater proportions of treatment responders in the higher dosing cohorts of EB-001. An IR-2 response was observed starting with Cohort 3 and increased in higher dose cohorts, suggesting that the efficacious dose range of EB-001 may be at doses used in Cohorts 4 to 7. Cohorts 6 and 7 had 80% IR-2 responders, a response rate similar to approved Botulinum toxin type A products. Subjects achieving none or mild FWS grades were observed starting at Cohort 2. In terms of onset of effect, treatment response was observed as early as 24 hours following dosing, which supports prior reports suggesting that Botulinum toxin type E has a faster onset than type A.

Regarding the duration of effect defined as the proportion of responders with a none or mild rating, an effect was observed through Day 14 in 1 subject in most of the 5 higher dose cohorts, and through Day 30 in 1 subject in 2 of the 5 higher dose cohorts. All doses of EB-001 showed good tolerability with no local injection site reactions. There were no SAEs or severe TEAEs reported, and no discontinuations due to a TEAE. The most common TEAE of headache was mild or moderate in severity, and there were no other treatment related AEs. There were no events of ptosis at any dose levels, and no events potentially related to spread of toxin. Therefore, the clinical safety and tolerability profile seems favorable in this study. The efficacy and safety profiles of EB-001 are promising and support the potential of EB-001 as a unique treatment option in the treatment of GL and other facial aesthetic uses. The fast onset can fulfill an unmet need for individuals seeking a rapid treatment for facial wrinkles before unexpected social or professional events. The limited duration of effect can be beneficial for individuals who may be considering first time use of a Botulinum neurotoxin treatment, and are unwilling to make a longer-term commitment. An EB-001 treatment would allow them to assess the aesthetic effect over a shorter duration of effect compared with the 12-week duration of effect of Botulinum toxin type A products. In this first clinical study in subjects with GL, EB-001 showed favorable safety and tolerability in all cohorts. Five out of the 7 cohorts showed numerically higher response rates compared to placebo, supporting the efficacy of EB-001 in the reduction of GL severity. The 2 highest doses provided an 80% response rate, similar to approved Botulinum toxin type A products. In contrast to the known time course of type A products, the clinical effect of EB-001 was seen within 24 hours (onset) and lasted between 14-30 days (duration). This differentiated clinical profile supports the future development of EB-001 for facial aesthetic and key therapeutic uses, where fast onset and short duration of effect are desirable.

TABLE S-1

| | Dose Escalation Scheme | | | |
|---|---|---|---|---|
| Cohort[1] | Total EB-001 Dose (ng)[2] | Dose at Procerus (ng) | Doses at Medial Corrugators (ng) | Dose at Lateral Corrugators (ng) |
| 1 | 0.1 | EB-001 (0.02) | EB-001 into right and left corrugators (0.02 each) | EB-001 into right and left corrugators (0.02 each) |
| 2 | 0.3 | EB-001 (0.06) | EB-001 into right and left corrugators (0.06 each) | EB-001 into right and left corrugators (0.06 each) |
| 3 | 0.9 | EB-001 (0.18) | EB-001 into right and left corrugators (0.18 each) | EB-001 into right and left corrugators (0.18 each) |
| 4 | 1.2 | EB-001 (0.24) | EB-001 into right and left corrugators (0.24 each) | EB-001 into right and left corrugators (0.24 each) |
| 5 | 1.6 | EB-001 (0.32) | EB-001 into right and left corrugators (0.32 each) | EB-001 into right and left corrugators (0.32 each) |
| 6 | 2.1 | EB-001 (0.42) | EB-001 into right and left corrugators (0.42 each) | EB-001 into right and left corrugators (0.42 each) |

TABLE S-1-continued

Dose Escalation Scheme

| Cohort[1] | Total EB-001 Dose (ng)[2] | Dose at Procerus (ng) | Doses at Medial Corrugators (ng) | Dose at Lateral Corrugators (ng) |
|---|---|---|---|---|
| 7 | 2.8 | EB-001 (0.56) | EB-001 into right and left corrugators (0.56 each) | EB-001 into right and left corrugators (0.56 each) |

Example 2

Use of Botulinum Toxin Type E to Treat Crows Feet

A 57 year old man with crow's feet resulting from years of sun exposure seeks treatment from his physician. The physician recommends a composition as disclosed herein, which is injected sub-dermally on either side of the patient's eyes. Each injection site receives about 3 units of type E botulinum toxin, with several injections made on either side of the eye. The crow's feet disappear within about 2 days after treatment, and remain reduced for two months.

Example 3

Use of Botulinum Toxin Type E for Brow Lift

A 60 year old woman presents with eyebrows extending below her brow bone. The physician recommends a composition as disclosed herein, which is injected subdermally above each eye. Each injection site receives about 10 units of type E botulinum toxin, with several injections made on either side of the eye. The drooping of the brow is reduced within about 2 days, and is substantially alleviated for 3 months after administration.

Example 4

Use of Botulinum Toxin Type E for Breast Augmentation

A 30 year old woman elects breast augmentation surgery. 4 hours prior to the procedure, botulinum toxin type E is administered in the proximity of where the surgical incisions will be made. The administration reduces muscle tension in the area of the incision, resulting in minimal scarring. Two weeks after the procedure, a supplemental dose is administered.

Example 5

Use of Botulinum Toxin Type E for Breast Reconstruction

A 30 year old woman elects breast reconstruction surgery. 14 hours prior to the procedure, botulinum toxin type E is administered in the proximity of where the surgical incisions will be made. The administration reduces muscle tension in the area of the incision, resulting in minimal scarring. Two weeks after the procedure, a supplemental dose is administered.

Example 6

Use of Botulinum Toxin Type E to Treat Episiotomy

A 44 year old woman undergoes an episiotomy. Immediately after the procedure, 4 ng of type E botulinum toxin to the tissue surrounding surgical area. Within 20 hours, muscle and nerve activity surrounding the wound is greatly reduced.

Example 7

Use of Botulinum Toxin Type E to Treat a Sports Hernia

A 28 year old man suffers a sports hernia. His doctor administers 4 ng of type E botulinum toxin to the tissue surrounding both the hernia. Within 10 hours, muscle and nerve activity surrounding the injury is greatly reduced.

Example 8

Use of Botulinum Toxin Type E to Treat a Shoulder Separation

A 48 year old man suffers a shoulder separation. His doctor administers 4 ng of type E botulinum toxin to the tissue surrounding both the hernia. Within 16 hours, muscle and nerve activity surrounding the injury is greatly reduced.

Example 9

Use of Botulinum Toxin Type E to Treat a Torn ACL

A 23 year old woman suffers a torn ACL. 6 hours after the injury, her doctor administers 7 ng of type E botulinum toxin to the muscle surrounding the torn ligament. Within 30 hours, muscle and nerve activity surrounding the wound is greatly reduced.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present disclosure, which is defined solely by the claims. Accordingly, embodiments of the present disclosure are not limited to those precisely as shown and described.

Certain embodiments are described herein, comprising the best mode known to the inventor for carrying out the methods and devices described herein. Of course, variations on these described embodiments will become apparent to those of ordinary skill in the art upon reading the foregoing description. Accordingly, this disclosure comprises all modifications and equivalents of the subject matter recited in the claims appended hereto as permitted by applicable law. Moreover, any combination of the above-described embodiments in all possible variations thereof is encompassed by the disclosure unless otherwise indicated herein or otherwise clearly contradicted by context.

Groupings of alternative embodiments, elements, or steps of the present disclosure are not to be construed as limitations. Each group member may be referred to and claimed individually or in any combination with other group members disclosed herein. It is anticipated that one or more members of a group may be comprised in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the disclosure are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the disclosure (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope otherwise claimed. No language in the present specification should be construed as indicating any non-claimed element essential to the practice of embodiments disclosed herein.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present disclosure so claimed are inherently or expressly described and enabled herein.

The invention claimed is:

1. A method for performing a cosmetic treatment on a human patient having glabellar lines, comprising administering by injection a total dose of between about 0.2 ng and about 20 ng of a botulinum neurotoxin serotype E to the patient,
wherein the total dose is divided into five approximately equal doses of the botulinum neurotoxin serotype E and the approximately equal doses are administered by intramuscular injection into the following muscles: procerus, left medial corrugator, right medial corrugator, left lateral corrugator, and right lateral corrugator, and
wherein the onset of clinical effect of the cosmetic treatment is obtained within 24 hours of administration of the botulinum neurotoxin serotype E.

2. The method of claim 1, wherein the botulinum neurotoxin serotype E is a pure about 150 kDa botulinum neurotoxin serotype E.

3. The method of claim 1, wherein the total dose comprises an amount of between about 2 ng and about 10 ng.

4. The method of claim 2, wherein the total dose is between about 0.2 ng and about 20 ng of the pure about 150 kDa botulinum serotype E.

5. The method of claim 1, wherein the clinical effect comprises an investigator-assessed Facial Wrinkle Scale (FWS) grade change at maximum frown from moderate to severe prior to the administration of the botulinum neurotoxin serotype E to none or mild following the administration of the botulinum neurotoxin serotype E.

6. The method of claim 5, wherein the total dose is between about 0.2 ng and about 20 ng of the pure about 150 kDa botulinum neurotoxin serotype E.

7. The method of claim 1, wherein about 150 U of the pure about 150 kDa botulinum neurotoxin serotype E is injected into at least one muscle.

8. A method for performing a cosmetic treatment on a human patient having moderate to severe glabellar lines, comprising administering a therapeutically effective amount of a pure about 150 kDa botulinum neurotoxin serotype E to the patient,
wherein the therapeutically effective amount is between about 0.2 ng and about 20 ng of the pure about 150 kDa botulinum neurotoxin serotype E,
wherein the therapeutically effective amount is administered in five intramuscular injections, each injection comprising an approximately equal amount of the pure about 150 kDa botulinum neurotoxin serotype E, wherein one injection is made into each of the following muscles: procerus, left medial corrugator, right medial corrugator, left lateral corrugator, and right lateral corrugator, wherein the onset of clinical effect of the cosmetic treatment is obtained within 48 hours following the administration of the pure about 150 kDa botulinum neurotoxin serotype E; and wherein the clinical effect comprises an investigator-assessed Facial Wrinkle Scale (FWS) grade change at maximum frown from moderate or severe prior to the administration of the pure about 150 kDa botulinum neurotoxin serotype E to none or mild following the administration of the pure about 150 kDa botulinum neurotoxin serotype E.

9. A method for performing a cosmetic treatment on a human patient having glabellar lines, comprising administering by injection a total dose of between about 0.2 ng and about 20 ng of a botulinum neurotoxin serotype E to the patient in the area where treatment is desired, wherein the total dose is divided into five approximately equal doses of the botulinum neurotoxin serotype E and the approximately equal doses are administered by intramuscular injection into the following muscles: procerus, left medial corrugator, right medial corrugator, left lateral corrugator, and right lateral corrugator, wherein the duration of clinical effect of the cosmetic treatment ranges from about 14 days to about 30 days following the administration of the botulinum neurotoxin serotype E, and wherein the clinical effect comprises an investigator-assessed Facial Wrinkle Scale (FWS) grade change at maximum frown from moderate or severe prior to the administration of the botulinum neurotoxin serotype E to none or mild following the administration of the botulinum neurotoxin serotype E.

10. The method of claim 9, wherein the botulinum neurotoxin serotype E is a pure about 150 kDa botulinum neurotoxin serotype E.

11. The method of claim 9, wherein the total dose comprises an amount of between about 2 ng and about 10 ng of the botulinum neurotoxin serotype E.

12. The method of claim 10, wherein the total dose is between about 0.2 ng and about 20 ng of the pure about 150 kDa botulinum neurotoxin serotype E.

13. The method of claim 9, wherein the method is statistically significantly better than a comparable method wherein a placebo is administered at achieving a 2-grade or better improvement (reduction) on the Facial Wrinkle Scale (FWS) assessment (IR-2) at maximum frown one (1), two (2), seven (7), 14, or 30 days after said administration.

14. The method of claim 13, wherein the total dose is between about 0.2 ng and about 20 ng of the pure about 150 kDa botulinum neurotoxin serotype E.

15. The method of claim 9, wherein about 150 U of the pure about 150 kDa botulinum neurotoxin serotype E is injected into at least one muscle.

16. A method for performing a cosmetic treatment on a human patient having moderate to severe glabellar lines, comprising administering a therapeutically effective amount of a pure about 150 kDa botulinum neurotoxin serotype E to the patient, wherein the therapeutically effective amount comprises a total dose in an amount of between about 2 ng and about 10 ng of the pure about 150 kDa botulinum neurotoxin serotype E, and wherein the therapeutically effective amount is administered in five intramuscular injections, each injection comprising an approximately equal amount of the pure about 150 kDa botulinum neurotoxin serotype E, wherein one injection is made into each of the following muscles: procerus, left medial corrugator, right medial corrugator, left lateral corrugator, and right lateral corrugator.

17. The method of claim 16, wherein the method is statistically significantly better than a comparable method wherein a placebo is administered at achieving a 2-grade or better improvement (reduction) on the Facial Wrinkle Scale (FWS) assessment (IR-2) at maximum frown one (1), two (2), seven (7), 14, or 30 days after said administration.

18. The method of claim 16, wherein about 150 U of the pure about 150 kDa botulinum neurotoxin serotype E is injected into at least one muscle.

* * * * *